US010183077B2

(12) United States Patent
Lacorte et al.

(10) Patent No.: US 10,183,077 B2
(45) Date of Patent: Jan. 22, 2019

(54) SOLID COMPOSITION COMPRISING IRON FOR USE IN IRON DEFICIENT CONDITIONS

(71) Applicant: ALESCO S.R.L., Pisa (IT)

(72) Inventors: Andrea Lacorte, Pisa (IT); Germano Tarantino, Pisa (IT)

(73) Assignee: ALESCO S.R.L., Pisa (IT)

(*) Notice: Subject to any disclaimer, the term of this patent is extended or adjusted under 35 U.S.C. 154(b) by 0 days.

(21) Appl. No.: 14/417,786

(22) PCT Filed: Jul. 30, 2013

(86) PCT No.: PCT/IB2013/001659
§ 371 (c)(1),
(2) Date: Jan. 27, 2015

(87) PCT Pub. No.: WO2014/009806
PCT Pub. Date: Jan. 16, 2014

(65) Prior Publication Data
US 2015/0250885 A1    Sep. 10, 2015

(30) Foreign Application Priority Data

Jul. 31, 2012   (IT) .............................. MI2012A1350

(51) Int. Cl.
| A61K 33/26 | (2006.01) |
| A61K 47/14 | (2017.01) |
| A61K 9/16 | (2006.01) |
| A61K 47/24 | (2006.01) |
| A61K 33/42 | (2006.01) |
| A61K 9/00 | (2006.01) |

(52) U.S. Cl.
CPC ............ *A61K 47/24* (2013.01); *A61K 9/0095* (2013.01); *A61K 9/1617* (2013.01); *A61K 9/1623* (2013.01); *A61K 9/1652* (2013.01); *A61K 33/26* (2013.01); *A61K 33/42* (2013.01); *A61K 47/14* (2013.01)

(58) Field of Classification Search
CPC ......... A61K 33/26; A61K 47/14; A61K 47/24
See application file for complete search history.

(56) References Cited

U.S. PATENT DOCUMENTS

| 6,083,529 A | 7/2000 | Manzo et al. |
| 2007/0148259 A1 | 6/2007 | Gupta |
| 2010/0008865 A1 | 1/2010 | Fayet et al. |
| 2012/0288531 A1* | 11/2012 | Tuvia ................ A61K 9/4858 424/400 |

FOREIGN PATENT DOCUMENTS

| JP | 2000-300213 A | 10/2000 | |
| JP | 2005-239693 A | 9/2005 | |
| JP | WO 2005082167 A1 * | 9/2005 | ............ A23L 1/0526 |
| JP | WO 2006137133 A1 * | 12/2006 | .............. A23L 5/41 |
| JP | 2007-215480 A | 8/2007 | |
| WO | 2005/082167 | 9/2005 | |

OTHER PUBLICATIONS

EPO machine translation of JP 4738410 B2 (Bibliographic data, claims, and description), counterpart to WO2006137133A1.*
International Preliminary Report on Patentability for PCT/IB2013/001659 filed on Jul. 30, 2013 in the name of Alesco S.R.L. dated Feb. 12, 2015. 7 pages.
PCT International Search Report dated Dec. 5, 2013 for PCT/IB2013/001659 filed on Jul. 30, 2013 in the name of Alesco S.R.L.
PCT Written Opinion dated Dec. 5, 2013 for PCT/IB2013/001659 filed on Jul. 30, 2013 in the name of Alesco S.R.L.
First Office Action for Chinese Patent Application No. 201380040500.1 dated Jun. 27, 2016. 8 pages (Chinese original + English translation).
Navas-Carretero, et al. "Iron absorption from meat pate fortified with ferric pyrophosphate in iron-deficient women" Nutrition; 2009; vol. 25; pp. 20-24.
Kis, et al. "Conference Abstract: The Potential of Sucrose Esters to be used as Oral Absorption Enhancers" Scientia Pharmaceutica, 2010; vol. 78, p. 716.
Tarantino, (2015) "Sucrosomial Iron®: a new highly bioavailable oral iron supplement", *Blood*, 126:4561. (2 pages).
Sochim International S.p.A. "Technical Data Sheet: Sunactive Fe-P80E" (1 page).
Japanese Office Action issued for Patent Application No. 2015-524859, dated Feb. 21, 2017. (5 pages; Chinese original + English Translation).

* cited by examiner

*Primary Examiner* — H. Sarah Park
(74) *Attorney, Agent, or Firm* — Steinfl+Bruno, LLP

(57) ABSTRACT

An iron-based composition is described. The composition can be used in conditions of total or relative iron deficiency. In particular, a solid composition is described, preferably in the form of powder or granules, for use in the treatment of disorders or diseases related to or derived from an iron deficiency. The composition is suitable for pediatric subjects, adolescents, athletes, men, women, pregnant women and elderly. Finally, a process for preparing the solid composition is also described.

12 Claims, No Drawings

SOLID COMPOSITION COMPRISING IRON FOR USE IN IRON DEFICIENT CONDITIONS

CROSS REFERENCE TO RELATED APPLICATIONS

The present application is the US national stage of International Patent Application PCT/IB2013/001659 filed on Jul. 30, 2013, which, in turn, claims priority to Italian Patent Application MI2012A001350 filed on Jul. 31, 2012.

The present invention relates to an iron-based composition, for use in conditions of total or relative iron deficiency. Specifically, the present invention relates to a solid composition, preferably in powder or granules form, for use in the treatment of disorders or diseases related to or derived from iron deficiency. The composition of the present invention is suitable for pediatric subjects, adolescents, athletes, men, women, pregnant women and elderly. Finally, the present invention relates to a process for preparing said solid composition.

It is known that iron therapy is an iron-based therapy suitable for conditions of total or relative iron deficiency in the body: in general terms, sideropenic anemias (including the iron supplementation to pregnant women).

Iron therapy can be carried out both orally, allowing an iron absorption through the intestinal uptake, and parenterally, allowing the absorption through a route other than the intestinal uptake, such as for example intramuscularly or intravenously. The iron therapy monitoring is conducted by hematochemical analyses such as for example hemogram and ferritin.

In the first event, by oral route, iron salt compositions (mainly ferrous sulphate or gluconate) are administered. However, oral (per os) administration of iron salt compositions has several limits and contraindications, which restrict the use thereof.

A first limit is that iron salts are poor absorbed. Therefore, in order to avoid a further reduction of absorption, iron salt compositions have to be administered between meals. However, buccal iron intake can cause constipation and epigastralgia leading to the need of administering the iron-based compositions under fed conditions with a consequent and inevitable severe reduction of absorption.

A second limit is that tolerability per os of iron salts, and in particular ferrous sulphate, is characterized by recurring gastrointestinal (GI) side effects, which in many cases limit the use thereof.

A third limit is that iron salt formulations, presently commercially available, have a reduced bioavailability. Therefore, besides a decreased absorption of iron (iron (II) or iron (III)) salts, there is also a reduced bioavailability of ferrous or ferric ion itself. Accordingly, the therapy based on iron (iron (II) or iron (III)) salts has to be prolonged over a long period of time and usually comprised from 3 to 6 months until the body iron deposits are successfully restored.

The above-mentioned limits represent only some of those more common and recurrent. The above-mentioned limits are considered to depend on how the known compositions based on iron (iron (II) or iron (III)) salts are prepared, the sequence of components being used and the selection thereof. Basically, an optimum preparation process is believed to be still established in order to create the suitable chemical-physical environment surrounding the cation iron (iron (II) or iron (III)), allowing the production of a convenient and superior composition.

Finally, the main contraindications deriving from the use of iron salt compositions are: peptic ulcer, gastritis, ulcerative colitis and malabsorption.

From the above, it is understood that the selection of iron salt type, iron (II) salt or iron (III) salt, the selection of compounds or substances used for formulating said salt and preparing the composition, and the selection of the kind of process employed for preparing the composition play a pivotal role.

It would be optimal to have an iron (II)- or iron (III)-based composition in which iron is highly bioavailable and, at the same time, devoid of any limits or drawbacks from the organoleptic point of view (taste, smell, color, long-term stability) and the composition is devoid of limits and disadvantages related to, for example, its hygroscopicity, particle agglomeration, color changing and its solubility.

However, water-soluble and bioavailable iron (II) salts, such as for example ferrous sulphate, often cause unacceptably color, taste, flavor and smell changes, in particular when said salts are mixed with other components or ingredients to form a final composition. On the other hand, iron (III) salts are less water-soluble and bioavailable than iron (II) salts, such as for example ferric pyrophosphate. The reduced bioavailability of, for example ferric pyrophosphate, is related to its moderate solubility in diluted acid, such as that present in gastric juice. Nevertheless, iron (III) salts, such as for example ferric pyrophosphate, have the advantage to be more stable and, thus, they change much less their smell, flavor and taste or their color, when said iron (III) salts are mixed with other components or ingredients to form a final composition.

Finally, liquid compositions or suspensions containing ferric pyrophosphate, being used for example in the treatment of iron deficiencies, suffer from the poor water-solubility of said iron (III) salt hindering the preparation of said compositions because, among others, an insoluble salt precipitate is very often formed, which hampers the dosage and use thereof.

Therefore, it would be desirable to have a novel iron (III) salt composition devoid of the limits and contraindications still existing in the present, commercially available compositions comprising iron (II) salts and iron (III) salts.

In particular, there is still a need to have a process for preparing an iron salt composition wherein iron (III) is effectively made readily absorbable and bioavailable; said process being capable to prepare an iron (III)-based composition which is well-tolerable so that it can be administered, even under fasting conditions, to all the subject categories including pregnant women, has a good palatability and is stable over time from the chemical-physical and organoleptic point of views, i.e. devoid of color, smell, flavor and taste changes.

The aim of the present invention is to provide a composition comprising iron (III) salts which is formulated and prepared such that the iron (III) salt is readily absorbable and bioavailable in an effective manner, the iron (III) salt is well-tolerated by the body in order to be administered, even under fasting conditions, to all the subject categories including pregnant women, the iron (III) salt has a good palatability and is stable over time from the chemical-physical and organoleptic point of views, i.e. devoid of color, smell, flavor and taste changes.

It is an object of the present invention a solid composition for use in the treatment of total or relative iron deficiencies, which comprises iron (III) salts, having the characteristics as disclosed in the appended claims.

It is an object of the present invention a solid composition, in powders or granules form, for use in the preventive or curative treatment of anemia or iron deficiency in women during both pregnancy and postnatal period, having the characteristics as disclosed in the appended claims.

It is another object of the present invention a process for preparing said solid composition, having the characteristics as disclosed in the appended claims.

It is another object of the present invention a composition in liquid or suspension form for use in the treatment of total or relative iron deficiencies, which comprises iron salts, having the characteristics as disclosed in the appended claims.

It is an object of the present invention a composition in liquid or suspension form for use in the preventive or curative treatment of anemia or iron deficiency in women during both pregnancy and postnatal period, having the characteristics as disclosed in the appended claims.

It is another object of the present invention a process for preparing said composition in liquid or suspension form, having the characteristics as disclosed in the appended claims.

Preferred embodiments of the present invention will be evident from the detailed description below.

The composition of the present invention is a solid-state composition. By solid state is meant that the composition of the present invention may exist in granules or powders form. The granulated or powdery compositions are then mixed with pharmacologically acceptable additives and excipients to provide a final product such as for example a supplement product, a medical device or a pharmaceutical composition. The final product can be in a pharmaceutical form such as, for example packet, tablet, pastille or capsule. The composition of the present invention, at solid state as granules or powders, has a bulk density (measured by equipment and methods well-known to the person skilled in the field) comprised from 0.3 to 0.8 g/ml, preferably from 0.4 to 0.7 g/ml and an iron (III) content comprised from 60 to 140 mg/g, preferably from 80 to 120 mg/g, even more preferably from 90 to 110 mg/g.

Tablets may have various shapes among those known in the pharmaceutical form field, such as for example a cylindrical or spheroidal shape. Tablets may have a weight comprised from 200 to 2000 mg. For example, a gel capsule may have a weight of 500 mg, a hard tablet may have a weight comprised from 800 to 1000 mg, whereas a chewable tablet may have a weight comprised from 1000 to 2000 mg. Capsules may consist of hard gelatin or soft gelatin or soft gel.

Tablets can be coated or filmed with one or more coating layers or films capable to pass through the gastric barrier. The coating is prepared by using a beeswax solution or a sugar-based solution.

The solid composition of the present invention is for oral use and can be a supplement product, a medical device or a pharmaceutical composition (briefly the solid composition of the present invention, for the sake of brevity).

The solid composition of the present invention comprises or, alternatively, consists of iron salts. Iron salts comprise or, alternatively, consist of iron III salts (ferric (III) salt).

Advantageously, the iron salts are iron (III) salts. Advantageously, the iron (III) salts comprise or, alternatively, consist of ferric pyrophosphate salts.

The solid composition of the present invention comprises an iron (III) pyrophosphate salt in an amount comprised from 30 to 70%, preferably from 40 to 60%, even more preferably from 50 to 55% by weight. In an embodiment, the ferric pyrophosphate being used $\{[Fe_4(P_2O_7)_3xH_2O]$, CAS 10058-44-3, dry molecular weight 745.22$\}$ is preferably in micronized form and has an iron content comprised from 18 to 24%, preferably from 20 to 22% by weight.

The solid composition of the present invention further comprises, combined with the iron (III) salt, a lecithin.

Lecithin is a food additive –E322 (Directive No. 95/2/EC of 20.2.95 published on O.J. No. L61 of 18 Mar. 1995). Lecithin, due to its chemical-physical properties, primarily plays an emulsifying function and, being also rich in natural antioxidant substances, has a secondary antioxidant function as well. Directive No. 2008/84/EC of 27 Aug. 2008 (published on European Community O.J. No. L253 establishes the purity criteria that lecithin have to present in order to be considered of food grade quality (E322): Acetone-insoluble (essentially the lecithin active part): 60% min.; Humidity: 2% max.; Acid number: 35 max.; Peroxide value: 10 max.; Toluene-insoluble (essentially impurities): 0.3% max.

From the chemical point of view, lecithin is a mixture of phosphoric acid, choline, fatty acids, glycerol, glycolipids, triglycerides and phospholipids. Phospholipids represent the main components thereof: they are derived from the triglyceride structure, wherein a fatty acid is replaced by a phosphate group, which confers a negative charge, and thus, polarity to the molecule; said molecule has the generic name of phosphatide. A more complex organic molecule, usually serine, choline, ethanolamine, inositol or a single hydrogen atom is bound through an ester bond to the phosphate group, giving rise to a phospholipid named phosphatidylserine, phosphatidylcholine, phosphatidylethanolamine, phosphatidylinositol or phosphatidic acid, respectively. In a more strict sense of lecithin, phosphatidylcholine is often designated. Phospholipids are characterized by a polar, water-soluble head, well-dissolving in water, whereas the two saturated fatty acids represent the two non polar, not water-soluble but lipophilic tails. Such kind of molecules are called amphipathic and in the presence of water and fats they arrange themselves between the fatty and water molecules emulsifying them. Lecithin is a natural emulsifier.

The solid composition for oral use of the present invention does not contain neither a hydrolyzed lecithin nor an enzymatically hydrolyzed lecithin.

The lecithin being used is a powdery non-hydrolyzed lecithin and can be selected from sunflower or maize or soya lecithin. The lecithin being used is a powdery lecithin having a water content comprised from 1.5 to 4.5%, preferably from 2 to 4%, even more preferably from 2.5 to 3.5%. Advantageously, the lecithin being used is a powdery sunflower lecithin.

In an embodiment, the sunflower lecithin has a glucose amount comprised from 20 to 60%, preferably from 30 to 50%, for example about 45% by weight, such as in the product Lecico Sun CG 450 from Lecico GmbH Company-Germany.

A sunflower lecithin usable in the context of the present invention may have the following composition by weight (chemical-physical analysis): sunflower lecithin from 40 to 50%, carbohydrates from 40 to 50% (for example about 42%), proteins from 6 to 10%, ashes from 3 to 8%, humidity from 2 to 5% and a glidant others from 0.5 to 1.5%.

Lecithin is in the solid composition of the present invention in an amount comprised from 0.1 to 1.5%, preferably from 0.4 to 1.0%, even more preferably from 0.50 to 0.8% by weight.

The solid composition of the present invention comprises or, alternatively, consists of iron (III) salts and a lecithin (neither non-hydrolyzed nor enzymatically hydrolyzed) in the above-cited amounts by weight. Advantageously, the iron (III) salt is ferric pyrophosphate and lecithin is from sunflower and/or maize.

The solid composition of the present invention comprises or, alternatively, consists of iron (III) salts from pyrophosphate and a sunflower lecithin (neither non-hydrolyzed nor enzymatically hydrolyzed) in the above-cited amounts by weight.

The solid composition of the present invention further comprises, combined with a lecithin disclosed above, a sucrose ester or sucrester.

Sucresters are obtained by fatty acid esterification or transesterification of fatty acid methyl esters with carbohydrates, generally sucrose and other polysaccharides, for this reason they are also referred to as fatty acid sucrose esters. The chemical-physical properties of these compounds depend on the number and type of esterified fatty acids. The abbreviation E473 means that sucresters are food additives permitted by the European Union legislation and regulated by ministerial decree (M.D. 1996). They are essentially emulsifiers and are added in order to obtain a better stabilization between an aqueous phase and a fatty phase.

Sucrose esters are sucresters (E473) and are used in the composition of the present invention at a HLB value of about 14-18, advantageously a HLB value of about 15 or 16, and used as emulsifiers.

In an embodiment sucrester E473 contains 70% of monoesters, being obtained by sucrose esterification with vegetable fatty acids (stearic and palmitic).

A sucrester usable in the context of the present invention may have the following composition by weight: total ester content at least 90%; free fatty acids (such as oleic acid) content not greater than 3%; free sucrose content not greater than 2%; humidity not greater than 4%; acid value not greater than 5. For example, sucrose esters SP70 from Chimab S.p.A Company-Italy.

Sucrose esters or sucresters exist in the solid composition in an amount comprised from 10 to 20%, preferably from 12.5 to 18.5%, even more preferably from 16 to 18.0% by weight.

The solid composition for oral use of the present invention does not contain neither a fatty acid ester nor diglycerol (diglycerol fatty acid ester).

The solid composition of the present invention comprises or, alternatively, consists of iron (III) salts, a lecithin E322 (neither non-hydrolyzed nor enzymatically hydrolyzed) and sucrose esters or sucresters E473 in an amount by weight as specified above.

The solid composition of the present invention comprises or, alternatively, consists of iron (III) salts from pyrophosphate, a sunflower lecithin (neither non-hydrolyzed nor enzymatically hydrolyzed) and sucrose esters or sucresters E473, in an amount by weight as specified above.

In a preferred embodiment, the solid composition of the present invention may further comprise a vegetable starch.

The vegetable starch is selected from rice starches or maize starches. Advantageously, the starch is rice starch. Advantageously, the rice starch is a gelatinized or pregelatinized native rice starch.

A pregelatinized rice starch usable in the context of the present invention may have the following chemical-physical characteristics: humidity not greater than 7%; protein content not greater than 1%; ash content not greater than 1%; pH (10% solution) comprised from 5.5 to 7.5, density 0.40-0.48 g/cm$^3$; content of starch minimum 97% and fats not greater than 0.1%. For example, a pregelatinized rice starch AX-FG-P of Reire Srl Company-Italy.

The gelatinized or pregelatinized vegetable starch is in the solid composition in an amount comprised from 15 to 40%, preferably from 20 to 35, even more preferably from 25 to 30 by weight.

The solid composition of the present invention comprises or, alternatively, consists of iron (III) salts, a lecithin E322 (neither non-hydrolyzed nor enzymatically hydrolyzed), sucrose esters or sucresters E473 and a vegetable starch, in the amounts by weight specified above.

The solid composition of the present invention comprises or, alternatively, consists of iron (III) salts from pyrophosphate, a sunflower lecithin (neither non-hydrolyzed nor enzymatically hydrolyzed), sucrose esters or sucresters E473 and a pregelatinized rice starch, in the amounts by weight specified above.

It is an object of the present invention a first method for preparing a solid composition of the present invention.

A first method of the present invention is directed to the preparation of a solid composition comprising or, alternatively, consisting of an iron (III) salt, a lecithin and a sucrose ester or sucrester, according to the above-described embodiments.

In a preferred embodiment, said first method also contemplates, when the iron (III) salt is contacted with lecithin and sucrose ester or sucrester E473, the use of a gelatinized or pregelatinized vegetable starch, having the characteristics as described above.

Said first method of the present invention comprises or, alternatively, consists of a series of processing steps through which the iron salt is coated or enveloped or encapsulated with said lecithin and/or said sucrose ester or sucrester and/or said vegetable starch.

The solid-state iron (III) salt, advantageously ferric pyrophosphate, is firstly contacted with said lecithin and then, secondly, with said sucrose ester or sucrester and/or said vegetable starch.

The salt at solid state as powder or granules has a water content of less than 3% by weight.

The iron salt containing the cation iron (III) is used in an amount comprised from 50 to 90%, preferably from 60 to 80%, even more preferably from 70 to 75% by weight.

Advantageously, the salt is an iron (III) salt. Advantageously, the iron (III) salt is ferric pyrophosphate having the characteristics as specified above.

The lecithin being used has the characteristics as described above. The contact time among the various components is comprised from 1 to 60 minutes, preferably from 10 to 50, even more preferably from 20 to 40 minutes.

The lecithin being used can be selected from sunflower or maize or soya lecithin. The lecithin being used is a powdery lecithin having a water content comprised from 1.5 to 4.5%, preferably from 2 to 4%, even more preferably from 2.5 to 3.5%. Advantageously, the lecithin used in said first method is a powdery, sunflower lecithin E322.

In said first method for preparing the solid composition for oral use of the present invention neither a hydrolyzed lecithin nor an enzymatically hydrolyzed lecithin is used.

The lecithin is in the solid composition of the present invention in an amount comprised from 0.1 to 1.5%, preferably from 0.4 to 1.0%, even more preferably from 0.50 to 0.8% by weight.

The lecithin, when contacted with said iron salt, arranges itself uniformly over said salt.

The gelatinized or pregelatinized vegetable starch is selected from rice starch or maize starch.

Advantageously, the starch is rice starch. Advantageously, the rice starch is a gelatinized or pregelatinized native rice starch. The vegetable starch has the characteristics as described above.

The starch is in the solid composition of the present invention in an amount comprised from 15 to 40%, preferably from 20 to 35%, even more preferably from 25 to 30% by weight.

The starch in the form of gelatinized or pregelatinized starch is advantageously more fluid and flowable and can be accurately dosed without causing errors or weight variations. Furthermore, it arranges itself in a more even and homogeneous manner. Finally, the pregelatinized starch enhances the bioavailability of the salt and thus, of the cation contained within said salt as the obtained compound is better dissolved at temperatures comprised from 15 to 30° C. (pressure 1 atmosphere), preferably from 20 to 25° C., even more preferably from 18 to 23° C.

Following to said first preparation method, a solid composition of the present invention is obtained, which comprises or, alternatively, consists of iron (III) salts, a sucrose ester or sucrester, a lecithin (neither non-hydrolyzed nor enzymatically hydrolyzed) and, preferably, a pregelatinized vegetable starch, in the amounts by weight specified above.

Particularly, by said first preparation method a solid composition of the present invention is obtained, which comprises or, alternatively, consists of iron (III) salts from pyrophosphate, a sunflower lecithin E322 (neither non-hydrolyzed nor enzymatically hydrolyzed), a sucrose ester or sucrester E473 and a pregelatinized rice starch, in the amounts by weight specified above.

The Applicant found that in order to further enhance the bioavailability of the salt and thus, of the cation contained within said salt, the amount by weight of lecithin to be used in the process for preparing the solid composition of the present invention has to be reduced as much as possible.

Moreover, the Applicant found that in order to further enhance the bioavailability of the salt and thus, of the cation contained within said salt, it is important to use a specific amount by weight of sucrose esters or sucresters in association with a reduced amount by weight of lecithin.

Advantageously, the sucrose ester or sucrester to lecithin ratio is comprised from 25:1 to 20:1. In an embodiment said ratio is comprised from 20:1 to 15:1.

It is an object of the present invention a second method for preparing a solid composition of the present invention.

A second method of the present invention is directed to the preparation of a solid composition comprising or, alternatively, consisting of an iron salt, sucrose esters or sucresters, a lecithin and a gelatinized or pregelatinized starch.

Said second method of the present invention comprises or, alternatively, consists of a technology developed in order to create a coating or encapsulation around iron so that to improve the cation stability and bioavailability.

Basically, said second method contemplates the formation of agglomerates or granules comprising the iron salt, sucrose esters or sucresters, lecithin and a gelatinized or pregelatinized starch. All of these components have the characteristics as specified above.

The sucrose esters or sucresters and lecithin act by enhancing the absorption of the salt and, accordingly, of the iron cation contained within said salt. The admixture with lecithin and starch gives rise to the formation of "chimeric" agglomerates capable to protect and shield the iron cation contained within said salt from gastric acid.

The iron salt containing the iron (III) cation is used in an amount comprised from 30 to 70%, preferably from 40 to 60%, even more preferably from 50 to 55% by weight.

The iron salt being used has the characteristics as described above. Advantageously, the salt is an iron (III) salt. Advantageously, the iron (III) salt is ferric pyrophosphate.

The processing time is comprised from 1 to 60 minutes, preferably from 10 to 50, even more preferably from 20 to 40 minutes.

The sucrose esters or sucresters are in an amount comprised from 10 to 30%, preferably from 15 to 25%, even more preferably from 16 to 20% by weight.

The lecithin being used is a maize or sunflower or soya lecithin. The lecithin being used is a powdery lecithin having a water content comprised from 1.5 to 4.5%, preferably from 2 to 4%, even more preferably from 2.5 to 3.5%. Advantageously, the lecithin being used is a powdery sunflower lecithin. The lecithin being used has the characteristics as specified above.

The lecithin is in an amount comprised from 0.1 to 1.5%, preferably from 0.4 to 1.0%, even more preferably from 0.5 to 0.8% by weight.

When lecithin is contacted with said granulate or powder, it arranges itself over the outer surface of granules or powders.

Thereafter, a gelatinized or pregelatinized vegetable starch selected from rice starch or maize starch is used. Advantageously, the starch is rice starch. Advantageously, the rice starch is a gelatinized or pregelatinized native rice starch. The starch being used has the characteristics as specified above.

The starch is in the solid composition of the present invention in an amount comprised from 15 to 40%, preferably from 20 to 35%, even more preferably from 25 to 30% by weight.

The gelatinized or pregelatinized starch is prepared according to the equipment and techniques known to the person skilled in the field. The rice flour gelatinization process aims to modify its technological properties bringing about a molecular rearrangement of the starchy component: said changes allow to provide a greater plasticity and viscosity to the mixtures and improve several characteristics of the products in which they are used. The properties obtained by gelatinization and the subsequent structural change of native starches contained in rice, allow the process to confer a faster hydration and a higher viscosity to flours. Moreover, the gelatinized starch strongly binds the water to the starchy matrix itself causing the latter to be less available. Accordingly, a longer storage time and a minor effect of chemical and enzymatic degradation phenomena are obtained. Pregelatinization is a physical technique (thus it does not contemplate adding other components) which modifies the starch properties and is based on cooking and subsequent drying of an aqueous native starch suspension (namely "rough" flour). The pregelatinized starches display the pivotal functional property of adsorbing a high amount of water, thus they are used as thickeners and gelling agents in several food formulations, especially when (and this is the case of rice or maize flours) the gluten protein fraction is absent. The cooking-extrusion (namely a short treatment at high temperatures and pressures) and drying carried out on cylinders represent the more common method for obtaining pregelatinization. In addition, pregelatinized starch-based products show good storage characteristics. This is because the water being present is strongly structured and captured within the pregelatinized starch matrix, whereby becoming not more available for degradation reactions, while at the same time the thermal treatment abolished some enzymatic (lipase and lipoxygenase) activities which often promote oxidative rancidity phenomena in "rough" flours and products derived therefrom.

In an embodiment, the lecithin is used in an amount comprised from 0.48 to 0.62% by weight, whereas sucrose esters or sucresters are used in an amount comprised from 16.5 to 18.5% by weight, relative to the weight of the final solid composition of the present invention. These combinations allow to enhancing the bioavailability of the cation contained within said salt of interest.

Following to said second preparation method, a solid composition of the present invention is obtained, which comprises or, alternatively, consists of iron (III) salts, sucrose esters or sucresters, a lecithin (neither non-hydrolyzed nor enzymatically hydrolyzed) and a pregelatinized vegetable starch, in the amounts by weight disclosed above.

Particularly, by said second preparation method, a solid composition of the present invention is obtained, which comprises or, alternatively, consists of iron (III) salts from pyrophosphate, sucrose esters or sucresters E473, a sunflower lecithin (neither non-hydrolyzed nor enzymatically hydrolyzed) and a pregelatinized rice starch, in the amounts by weight disclosed above.

The solid composition of the present invention has a particle size (that is understood as average particle size measured by available equipment and techniques) comprised from 8 to 16 microns, preferably from 10 to 14 microns, even more preferably from 11 to 13 microns. The solid composition of the present invention has an iron (III) content comprised from 60 mg/g to 140 mg/g, preferably from 80 mg/g to 120 mg/g, even more preferably from 90 to 110 mg/g.

The solid composition being obtained is for use in conditions of total or relative iron deficiency, in particular for use in the treatment of disorders or diseases related to or derived from iron deficiency.

The solid composition of the present invention, obtained as described above, is for use in conditions of total or relative iron deficiency, in particular for use in the treatment of disorders or diseases related to or derived from iron deficiency.

Advantageously, the composition of the present invention comprising iron (III) salts is prepared through the above-described method (said first and second methods) so that the iron (III) salt showed to be readily absorbable and bioavailable in an effective manner. In addition, the iron (III) salt showed to be well-tolerated by the body. Advantageously, the composition of the present invention can be administered, even under fasting conditions, to all of the subject categories including pregnant women. Advantageously, the iron (III) salt as prepared in the composition of the present invention has a good palatability and showed to be stable over time from a chemical-physical and organoleptic point of views namely, when subjected to stability tests, the iron (III) salt did not bring about color, smell, flavor and/or taste changes.

It is an object of the present invention a liquid composition for use in the treatment of total or relative iron deficiencies, as described below.

The liquid composition for oral use of the present invention may exist as liquid, suspension or syrup form.

The liquid composition of the present invention is for oral use and can be a supplement product, a medical device or a pharmaceutical composition (briefly, the liquid composition of the present invention, for the sake of brevity).

The liquid composition of the present invention comprises or, alternatively, consists of water, iron (III) salts, a lecithin as described above, sucrose esters or sucresters as described above and guar gum. All of these components have the characteristics and chemical-physical properties, as disclosed above.

The liquid composition of the present invention does not contain neither a hydrolyzed lecithin nor an enzymatically hydrolyzed lecithin.

The liquid composition of the present invention does not contain neither a fatty acid ester nor diglycerol (diglycerol fatty acid ester).

The liquid composition of the present invention has a viscosity (measured under standard conditions and by well-known equipment and techniques) comprised from 1.01 to 1.12 g/ml, preferably from 1.02 to 1.10 g/ml, even more preferably from 1.03 to 1.08 g/ml.

The liquid composition of the present invention comprises iron salts, having the characteristics as disclosed above. The iron salts are iron III salts (ferric (III) salt). Advantageously, the iron (III) salt is ferric pyrophosphate.

The liquid composition of the present invention contains an iron salt in an amount comprised from 1 to 10%, preferably from 2 to 8%, even more preferably from 4 to 6% by weight, relative to the weight of the liquid composition.

The liquid composition of the present invention further comprises sucrose esters or sucresters, having the characteristics as described above.

Sucrose esters or sucresters E473 are in said liquid composition of the present invention in an amount comprised from 0.10 to 5%, preferably from 0.5 to 4%, even more preferably from 1 to 3% by weight, relative to the weight of the liquid composition.

The liquid composition of the present invention further comprises a lecithin, having the characteristics as described above.

Lecithin E322 being used can be selected from sunflower or maize or soya lecithin. Advantageously, the lecithin being used is a sunflower lecithin.

In an embodiment, the sunflower lecithin contains a glucose amount comprised from 20 to 60%, preferably from 30 to 50%, for example 45% by weight as in the product Lecico Sun CG 450 of Lecico GmbH Company-Germany.

A sunflower lecithin usable in the context of the present invention may have the following composition by weight (chemical-physical analysis): sunflower lecithin from 40 to 50%, carbohydrates from 40 to 50% (for example, carbohydrates 42%), proteins from 6 to 10%, ashes from 3 to 8%, humidity from 2 to 5% and a glidant others from 0.5 to 1.5%.

The lecithin is in said liquid composition in an amount comprised from 0.1 to 4%, preferably from 0.5 to 3.5%, even more preferably from 1.5 to 2.5% by weight, relative to the weight of the liquid composition.

The liquid composition of the present invention further comprises a guar gum.

The guar gum is in said liquid composition of the present invention in an amount comprised from 0.1 to 5%, preferably from 0.2 to 4%, even more preferably from 0.4 to 2% by weight, relative to the weight of the liquid composition.

In an embodiment, the guar gum is selected from those commercially available and has a viscosity (cPs, 2 hours) comprised from 3000-4500, preferably from 3500 to 4000; starch-free; with a content of acid-insoluble substances comprised from 5 to 9, preferably from 6 to 8, for example 7; with a R.U.A comprised from 2.5 to 4%, preferably from 3 to 3.5% and a particle size comprised from 100 to 300, preferably from 150 to 250, for example 200.

It is an object of the present invention a process for preparing said liquid composition comprising or, alternatively, consisting of a technology capable to yield a time-stable composition or emulsion or suspension depending on the operational conditions being used. The process provides a liquid composition devoid of deposit (precipitates or agglomerates in suspension) and having an even and sustained concentration over time.

In an embodiment, the water is in an amount of 90%, or 92%, or 94% by weight. The water is kept under stirring at a temperature comprised from 15 to 45° C. (pressure 1 atmosphere), preferably from 20 to 35° C., even more preferably from 25 to 30° C.

Next, the sucrose esters or sucresters, lecithin, guar gum and iron (III) salts (having the characteristics as disclosed above) are added in the amounts specified below. Sucrose esters or sucresters are in an amount comprised from 0.10 to 5%, preferably from 0.5 to 4%, even more preferably from 1 to 3% by weight, relative to the weight of the liquid composition.

Water and sucrose esters or sucresters form a clear solution/suspension at a temperature comprised from 15 to 45° C. (pressure 1 atmosphere), preferably from 20 to 35° C., even more preferably from 25 to 30° C.

The processing time is comprised from 1 to 60 minutes, preferably from 10 to 50 minutes, even more preferably from 20 to 40 minutes.

The lecithin (having the characteristics as disclosed above) is used in an amount comprised from 0.1 to 4%, preferably from 0.5 to 3.5%, even more preferably from 1.5 to 2.5% by weight, relative to the weight of the liquid composition.

Water, sucrose esters or sucresters and lecithin form a clear solution/suspension at a temperature comprised from 15 to 45° C. (pressure 1 atmosphere), preferably from 20 to 35° C., even more preferably from 25 to 30° C.

The guar gum (having the characteristics as disclosed above) is used in an amount comprised from 0.1 to 5%, preferably from 0.2 to 4%, even more preferably from 0.4 to 2% by weight, relative to the weight of the liquid composition.

Water, sucrose esters or sucresters, lecithin and guar gum form a clear solution/suspension at a temperature comprised from 15 to 45° C. (pressure 1 atmosphere), preferably from 20 to 35° C., even more preferably from 25 to 30° C.

Said iron salt (having the characteristics as disclosed above) is in an amount comprised from 1 to 10%, preferably from 2 to 8%, even more preferably from 4 to 6% by weight, relative to the weight of the liquid composition.

At the end of the processing, an opalescent solution or a homogeneous suspension is obtained. The working temperature is comprised from 15 to 45° C. (pressure 1 atmosphere), preferably from 20 to 35° C., even more preferably from 25 to 30° C. The processing time is comprised from 1 to 60 minutes, preferably from 20 to 50 minutes, even more preferably from 30 to 40 minutes.

Next, the liquid composition undergoes a thermal treatment, for example pasteurization. Basically, the liquid composition being at a temperature comprised from 20 to 25° C. is heated at a temperature of about 110° C. and then cooled down at a temperature of about 25-30° C. The thermal treatment step is carried out over a period of time comprised from 1 to 3 minutes.

Following to said process for preparing said liquid composition, the liquid composition of the present invention is obtained, which comprises or, alternatively, consists of water, iron (III) salts, sucrose esters or sucresters, a lecithin (neither non-hydrolyzed nor enzymatically hydrolyzed) and a guar gum, in the amounts by weight specified above.

In particular, by said preparation process, the liquid composition of the present invention is obtained, which comprises or, alternatively, consists of water, iron (III) salts from pyrophosphate, sucrose esters or sucresters E473, a sunflower lecithin (neither non-hydrolyzed nor enzymatically hydrolyzed) and a guar gum, in the amounts by weight specified above.

In an embodiment of the present invention, the solid compositions obtained by said first and second methods as disclosed above, can be added of water together with guar gum to form the liquid composition of the present invention.

Advantageously, the liquid composition of the present invention comprising iron (III) salts is prepared such that the iron (III) salt showed to be readily absorbable and bioavailable in an effective manner. Moreover, the iron (III) salt showed to be well-tolerated by the body. Advantageously, the liquid composition of the present invention can be administered, even under fasting conditions, to all of the subject categories including pregnant women. Advantageously, the iron (III) salt as prepared in the liquid composition of the present invention has a good palatability and showed to be stable over time from a chemical-physical and organoleptic point of views namely, when subjected to stability tests, the iron (III) salt did not give rise to color, smell, flavor and/or taste changes. Furthermore, the liquid composition of the present invention does not originate precipitates, agglomerates or opalescence as it is highly stable.

The solid compositions for oral use of the present invention, obtained by said first and second methods, are solid-state (granules or agglomerates or powders) raw materials which are then mixed with pharmacologically acceptable additives and excipients to give pharmaceutical forms for oral use such as tablets, pastilles, capsules, packets.

The liquid composition for oral use of the present invention is mixed with pharmacologically acceptable flavorings, excipients and additives to form a syrup or liquid suspension for oral use.

Advantageously, the supplement product or medical device or pharmaceutical composition for oral use comprising the solid or liquid composition for oral use according to any one of the above-described embodiments, is successfully used in the treatment of disorders or diseases related to iron deficiency in pediatric subjects, adolescents, athletes, men, women, pregnant women and elderly since they prevent anemia and are useful for increasing hemoglobin and ferritin values. Said supplement product or medical device or said pharmaceutical composition, in solid form or liquid form, according to any one of the above-disclosed embodiments is suitable for administration over a period comprised from 1 to 5 months, preferably from 2 to 4 months. Advantageously, said supplement product or medical device or said pharmaceutical composition, in solid form or liquid form, for use in pediatric subjects, adolescents, athletes, men, women, pregnant women and elderly, is suitable at a dose comprised from 10 to 40 mg of iron (III)/day, preferably from 14 to 30 mg of iron (III)/day, even more preferably 28 mg of iron (III)/day.

Advantageously, the solid and liquid compositions of the present invention are suitable for pregnant women as they increase the birth weight of the newborn, prevent maternal anemia and efficiently affect the hemoglobin and ferritin values.

In an embodiment of the present invention the solid and liquid compositions are administered throughout the pregnancy period, in particular starting from $12^{th}$ week, until 6 weeks postnatal (postpartum). The recommended dose is comprised from 10 to 40 mg/day, preferably from 14 to 30 mg/day, advantageously 28 mg/day.

Experimental Part

The Applicant conducted an in vivo study in order to test the properties of the solid and liquid compositions of the present invention and compare said properties to those of other commercially known products.

The results relate to a step of the study (4 animals/group) aiming to compare the effect of different iron-containing formulations to some hematological parameters in the rat.

The study was performed by using male Sprague-Dawley rats, weighing about 250-300 g (average weight 275±3; n=16). The animals, housed in a thermostatic environment (22° C.) and under a 12 hour light cycle (from h 6 to h 18), had free access to water and food.

The study was carried out according to the European Community directives (86/609/EEC), the guide lines issued by the Ministry of Health (LD 116/92; LD 111/94-B) and approved by the local Ethics Committee of the institute that performed the study. The study was subdivided into two steps.

In the first step the iron serum levels following to a single oral administration (0.5 mg of iron/Kg) of the tested products were assessed.

In the second step, the effects of a daily oral administration over 30 days (0.5 mg iron/kg) of the tested products to 4 parameters were assessed: serum iron, hemoglobin, ferritin and transferrin saturation percentage.

First step: single bolus administration (0.5 mg of iron/Kg).

The rats divided in 4 experimental groups (4 animals/group) were administered with the following formulations:
  i) Vehicle (carboxymethyl cellulose 1%; control group)
  ii) Iron sulphate-based product
  iii) Liquid composition of the present invention
  iv) Solid composition of the present invention The liquid composition (iii) comprises (100 ml): purified water (94.297 g), iron pyrophosphate (4.892 g), sunflower lecithin (1.854 g), sucrose esters or sucresters (1.236 g) and guar gum (*Cyamopsis Tetragonoloba*) (0.721 g). The density is equal to 1.03 g/ml=100 ml by volume and 103 g by mass.

The solid composition (iv) comprises (100 g): iron pyrophosphate (53.71 g), pregelatinized rice starch (28.57 g), sucrose esters or sucresters (17.14 g) and sunflower lecithin (0.58 g). The iron (III) content is 112.791 mg.

Each animal from every group was subjected to 8 blood withdrawals (100-200 µl/withdrawal): time zero (before administration), 30 minutes and 1, 2, 4, 6, 8 and 12 hours from administration of formulations (i)-(iv). In each blood sample the serum iron levels were measured by atomic absorption.

The results show that the control group has an average value of about 1.50 mg/ml, within the range between 30 and 120 minutes from administration.

The formulations (iii) and (iv) of the present invention have a peak for iron serum levels greater than 35%, relative to the average value of control group, immediately after 30 minutes from administration. Furthermore, the peak remains at constant values over additional 90 minutes (overall 120 minutes from administration) prior to starting to decrease. This trend is absent in formulation (ii).

Formulation (ii) has a peak after 30 minutes from administration of less of about 30% (relative to formulations (iii) and (iv)), then increases after additional 30 minutes up to a value of less of about 20% (relative to formulations (iii) and (iv)), and thus decreases after further 60 minutes to a value of less of about 25% (relative to formulations (iii) and (iv)).

Thus, formulations (iii) and (iv) have a higher and more constant peak over time than formulation (ii).

Second step: administration of a once-daily bolus (0.5 mg of iron/Kg) over 30 days. Rats subdivided in 4 experimental groups (4 animals/group) were administered with formulations (i)-(iv).

At time 1 (first bolus administration) and after 15 and 30 days of administration of formulations (i)-(iv) serum iron, hemoglobin, ferritin and transferrin saturation percentage were measured. The withdrawals were taken after one hour from administration, at the hematic peak of iron, observed in the first step.

The values measured in samples withdrawn at time 1, 15 days and 30 days of treatment (1 hour following to the bolus administration) for serum iron (mg/l), hemoglobin (g/dl), ferritin (µg/l) and transferrin saturation percentage (%) show that formulations (iii) and (iv) provide higher and more constant values than those obtained from formulation (ii).

The Applicant performed an in vivo study in order to assess the effects of different regimens of iron administration to the iron status and the ongoing of pregnancy of pregnant women.

The aim of the study was to assess the effects of different iron doses and regimens to the ongoing of pregnancy and the maternal hematological parameters.

80 non-anemic pregnant women (hemoglobin Hb>10.5 g/dL) from $12^{th}$ to $14^{th}$ weeks of gestation were recruited and randomly divided into 4 groups of 20 subjects: control (C; n=20) and 3 additional groups with iron (II) 30 mg/day (FI; n=20), the solid iron (III)-based composition of the present invention being prepared according to said first or second method at 14 mg/day, a commercially present supplement product named SIDERAL® marketed by Pharmanutra S.r.l Company-Italy, (LI 14; n=20) and the solid iron (III)-based composition of the present invention being prepared according to said first or second method at 28 mg/day, a commercially present supplement product named SIDERAL® marketed by Pharmanutra S.r.l Company Italy, (LI 28; n=20); all the groups were treated until 6 weeks postnatal. Data and parameters of the subjects were collected during the recruiting, at $20^{th}$ week, $28^{th}$ week and 6 weeks postnatal by means of questionnaires, anthropometric measurements and blood sample withdrawals.

The results of the study showed that the groups were homogeneous by maternal age (average value 30.2±1.2 years) and BMI (average value 22.8±1.6 kg/m²).

The group LI 28 shows significantly higher Hb levels than both control (p<0.01) and FI (p<0.05) at 28 weeks and during the postpartum period of 6 weeks.

Ferritin levels were significantly higher in group LI 28, at 20 weeks (p=0.05), 28 weeks and 6 weeks postpartum (p<0.01) than control. The drop-out for anemia was: C n=6, FI n=5, LI 14 n=5, LI 28 n=2. In addition, the birth weight resulted to be significantly higher in group LI 28 than control (3479±587 vs 3092±469 g, p<0.05). Whereas the placenta weight, bleeding and gestation period were similar in all the groups.

The data show that the solid composition of the present invention at 28 mg/day increases the birth weight of the newborn and prevents maternal anemia. Similar known results were previously obtained with 40 mg/day of an iron (II)-based compound. Furthermore, the present study shows that group LI 14 (14 mg/day of iron (III)—the solid composition of the present invention) yields the same results of group FI (30 mg/day of iron (II)—iron (II)-based compound with regards to the hematological parameters, whereby the solid composition of the present invention allows to reducing both the iron dose to be administered and the side effects.

The invention claimed is:

1. A method for treating a subject, the method comprising: administering to the subject a solid composition comprising an iron (III) salt, said iron (III) salt being ferric pyrophosphate, in an amount from 30% to 70% by weight, sucrose esters or sucresters E473, wherein said sucrose esters or sucresters E473 are in an amount from 10% to 30% by weight, and a non-hydrolyzed lecithin, wherein said lecithin is in an amount from 0.1% to 1.5% by weight in an effective amount to treat iron deficiency in the subject.

2. The method according to claim 1, wherein said composition further comprises a gelatinized or pregelatinized starch.

3. The method according to claim 1, wherein said lecithin is a lecithin E322 and is selected from the group comprising the maize, sunflower or soya lecithin.

4. The method according to claim 1, wherein said sucrose ester or sucrester and said lecithin are in the composition in a weight ratio from 25:1 to 20:1.

5. The method according to claim 2, wherein said gelatinized or pregelatinized starch is selected from the group consisting of rice starch and maize starch, said starch in an amount from 15 to 40% by weight.

6. The method according to claim 2, wherein the iron (III) salt is ferric pyrophosphate in an amount from 50 to 55% by weight; the lecithin is sunflower lecithin in an amount from 0.5 to 0.8 by weight; the sucrester E473 is in an amount from 16 to 20% by weight; and the gelatinized or pregelatinized starch is rice starch in an amount from 25 to 30% by weight.

7. The method according to claim 1, wherein said solid composition for oral use has a particle size from 8 to 16 microns, a bulk density from 0.3 to 0.8 g/ml, and an iron (III) content from 60 mg/g to 140 mg/g.

8. The method according to claim 1, wherein said iron (III) salt is in an amount from 40 to 60% by weight.

9. The method according to claim 1, wherein said sucrose esters or sucresters E473 are in an amount from 15 to 25% by weight.

10. The method according to claim 1, wherein said lecithin is in an amount from 0.4 to 1% by weight.

11. The method according to claim 4, wherein said sucrose ester or sucrester and said lecithin are in the composition in a weight ratio from 20:1 to 15:1.

12. The method according to claim 7, wherein said solid composition for oral use has a particle size from 10 to 14 microns, a bulk density from 0.4 to 0.7 g/ml, and an iron (III) content from 80 mg/g to 120 mg/g.

* * * * *